United States Patent
Bodner et al.

(10) Patent No.: US 7,184,841 B1
(45) Date of Patent: Feb. 27, 2007

(54) PACING LEAD STABILIZER

(75) Inventors: Jeffrey P. Bodner, St. Paul, MN (US); Luis M. Rodriguez, Shoreview, MN (US); David B. Yingling, Stillwater, MN (US); Yvo A. Yrimia, San Juan, PR (US); Matthew C. Laabs, Blaine, MN (US); Matthew S. Finlay, Brooklyn Park, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 352 days.

(21) Appl. No.: 10/921,520

(22) Filed: Aug. 19, 2004

(51) Int. Cl.
*A61N 1/00* (2006.01)
(52) U.S. Cl. ...................... 607/122; 607/132
(58) Field of Classification Search ................ 607/119, 607/122, 125, 132
See application file for complete search history.

(56) References Cited

U.S. PATENT DOCUMENTS

| | | |
|---|---|---|
| 4,516,584 A | 5/1985 | Garcia |
| 4,553,961 A | 11/1985 | Pohndorf et al. |
| 4,672,979 A | 6/1987 | Pohndorf |
| 4,683,895 A | 8/1987 | Pohndorf |
| 5,152,298 A | 10/1992 | Kreyenhagen et al. |
| 5,242,431 A | 9/1993 | Kristiansen |
| 5,273,053 A * | 12/1993 | Pohndorf .................... 607/132 |
| 5,423,763 A | 6/1995 | Helland et al. |
| 5,476,493 A | 12/1995 | Muff |
| 5,603,730 A | 2/1997 | Romkee |
| 5,683,403 A | 11/1997 | Adams et al. |
| 5,709,644 A | 1/1998 | Bush |
| 5,735,891 A | 4/1998 | White |
| 5,746,722 A * | 5/1998 | Pohndorf et al. ........... 604/175 |
| 5,957,968 A * | 9/1999 | Belden et al. .............. 607/126 |
| 6,473,654 B1 | 10/2002 | Chinn |
| 2002/0138041 A1 | 9/2002 | Zhang et al. |
| 2003/0050668 A1 | 3/2003 | Lee |
| 2004/0059403 A1 | 3/2004 | Massullo |

* cited by examiner

*Primary Examiner*—Robert E. Pezzuto
*Assistant Examiner*—Brian T. Gedeon
(74) *Attorney, Agent, or Firm*—Faegre & Benson LLP (57) ABSTRACT

A lead assembly for use with an implantable cardiac function management system. The lead assembly includes an elongated flexible pacing lead having a proximal end and a distal end. A terminal connector is connected to the proximal end of the pacing lead and has a distal end formed with a first coupling feature. A pacing lead stabilizer having a central bore is mounted on the pacing lead and is slidable along the pacing lead. The pacing lead stabilizer has a stabilizer proximal end formed with a mating feature complementary to the first coupling feature, such that the pacing lead stabilizer is releasably coupleable to the terminal connector.

27 Claims, 9 Drawing Sheets

PACING LEAD STABILIZER

TECHNICAL FIELD

The present invention is related to implantable medical devices and, in particular, to a lead assembly for a cardiac pacing device having a pacing lead stabilizer for attaching the lead to surrounding tissue.

BACKGROUND

Pacing lead assemblies are typically implanted in the vasculature so that a surface electrode coupled to a distal end of the pacing lead is positioned in or near the heart. A proximal end of the pacing lead is coupled via a terminal boot or terminal connector to a pulse generator implanted in a pocket formed underneath the skin, usually in the patient's abdominal or upper chest region. The pacing lead extends from the pulse generator through an aperture in an access vessel, along the access vessel and into the heart.

Patient movement and cardiac contractions may dislodge the pacing lead from its implanted position. Movement of the pacing lead can exert tension on the pulse generating device and may cause patient discomfort. To prevent movement of the lead, the lead is typically sutured to the surrounding tissue via a pacing lead stabilizer. U.S. Pat. No. 5,957,968 (Belden et al.) describes an exemplary suture sleeve or anchoring sleeve for securing an electrical lead in place. As disclosed in Belden, the sleeve was sutured to adjacent tissue, and then the lead was snapped into the sleeve to secure the lead in place.

Suture sleeves of the prior art were typically bulky and sometimes were visible or palpable below the surface of the skin. Sometimes during implantation, the suture sleeve would slide distally along the lead body through the aperture and into the access vessel and become "lost." Retrieving the suture sleeve could be a difficult, time consuming and potentially dangerous process. Also, such suture sleeves were sometimes difficult to manipulate during the implantation process. There is thus a need in the art for a pacing lead assembly having a pacing lead stabilizer with a low profile that is easily positioned and manipulated during implantation.

SUMMARY

According to a first embodiment, the present invention is a lead assembly for use with an implantable cardiac function management system. The lead assembly includes an elongated flexible pacing lead having a proximal end and a distal end. A terminal connector is connected to the proximal end of the pacing lead and has a distal end formed with a first coupling feature. A pacing lead stabilizer having a central bore is mounted on the pacing lead and is slidable along the pacing lead. The pacing lead stabilizer has a stabilizer proximal end formed with a mating feature. The mating feature is complementary to the first coupling feature such that the pacing lead stabilizer is releasably coupleable to the terminal connector. In one embodiment, the first coupling feature is an annular ridge and the mating feature is an annular recess formed in the bore at the stabilizer proximal end. The annular ridge is receivable in the annular recess.

According to another embodiment, the present invention is a lead assembly for use with an implantable cardiac function management system. The lead assembly includes an elongated flexible pacing lead, a pacing lead stabilizer and a separable anchor mechanism means. The pacing lead has an electrode at a distal end and a terminal connector at a proximal end. The pacing lead stabilizer has a central bore and is coupled to the lead such that the lead extends through the central bore. The separable anchor mechanism means restricts linear movement of the pacing lead stabilizer with respect to the pacing lead. According to one embodiment, the anchor mechanism means is a separable mechanical interlock coupling the pacing lead stabilizer to the terminal connector.

According to yet another embodiment, the present invention is a method of implanting a pacing lead assembly. The pacing lead assembly includes a pacing lead, a pacing lead stabilizer and an anchor mechanism. The pacing lead has a surface electrode at a distal end and a terminal connector at a proximal end. The pacing lead stabilizer has a central bore slidably mounted to the pacing lead. The anchor mechanism restricts linear motion of the pacing lead stabilizer with respect to the pacing lead. The distal end of the pacing lead is inserted through an aperture in an access vessel to the heart. The pacing lead is advanced through the access vessel until the distal end of the pacing lead is positioned in or near the heart. The anchor mechanism is separated to allow full linear motion of the pacing lead stabilizer with respect to the pacing lead. The pacing lead stabilizer is located at an appropriate position along the pacing lead for securing the pacing lead to the surrounding tissue. The pacing lead stabilizer is sutured to the surrounding tissue and to the pacing lead to resist dislocation of the lead. According to one embodiment, the pacing lead stabilizer is retained adjacent the terminal connector throughout insertion and advancement of the pacing lead through the access vessel.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
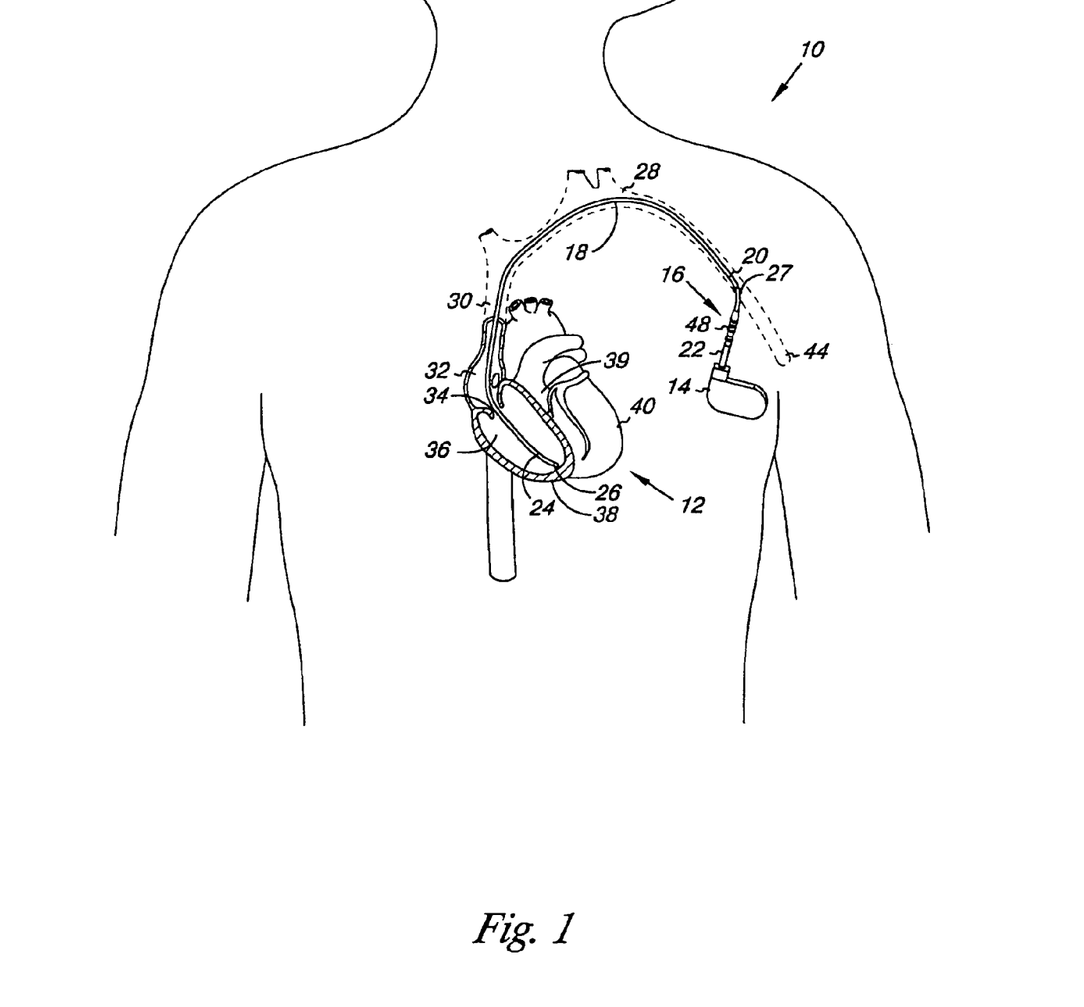
FIG. 1 is a schematic view of an implantable medical device that can be used in relation to embodiments of the present invention and a portion of the vasculature.

FIG. 1 shows an implantable cardiac function management system 10 for delivering a treatment or therapy to a human heart 12. The cardiac function management system 10 may, for example, be a pacemaker, an implantable cardioverter defibrillator (ICD), or a cardiac resynchronization device. The system 10 includes a pulse generator 14 implanted in a pocket formed underneath the skin in the upper chest. However, the pulse generator 14 may be planted elsewhere as is known in the art, for example, the abdominal area. The system 10 further includes a cardiac lead assembly 16 coupled to the pulse generator 14 and extending into the heart 12. The pulse generator 14, in one embodiment, includes a power source, circuitry for receiving and delivering electrical signals through the cardiac lead assembly 16, and circuitry for determining an appropriate therapy.

As further shown in FIG. 1, the lead assembly 16 includes a flexible elongated lead body 18 coupled at a proximal end 20 to the pulse generator 14 via a terminal connector 22 and coupled at a distal end 24 to a surface electrode 26 as is known in the art. In one embodiment, the lead body 18 extends from the pulse generator 14 through an aperture 27 in the left subclavian vein 28, along the left subclavian vein 28, through the superior vena cava 30, into the right atrium 32, through the tricuspid valve 34, and into the right ventricle 36 of the heart 12. The surface electrode 26 is positioned in the right ventricle 36 near the apex 38 of the heart 12. When positioned as above, the electrode 26 can be used to sense the electrical activity of the heart 12 or to apply a stimulating pulse to the right ventricle 36.

In other embodiments, the cardiac lead assembly 16 of the present invention can also be implanted in any other portion of the heart 12 as known in the art of cardiac function management and the lead assembly 16 may extend along any appropriate access vessel into the heart 12. For example, the lead assembly 16 may be implanted in the right atrium 32, the left atrium 39 or the left ventricle 40, and the lead assembly 16 may extend along appropriate access vessels thereto, for example the left axillary vein 44. In one embodiment, the lead assembly 16 is an epicardial lead assembly attached to the epicardium or within the myocardium, as is known in the art.

Following placement of the lead assembly 16 into the heart 12, the proximal end 20 of the lead body 18 is secured to adjacent tissue to resist dislocation of the lead assembly 16. To secure the lead body 16, a pacing lead stabilizer such as an anchor or suture sleeve 48 is slidably mounted to the lead body 18. Following implantation, the pacing lead stabilizer 48 is coupled to surrounding tissue to secure the lead body 18 in place. In one embodiment, the pacing lead stabilizer 48 is sutured to surrounding tissue. In another embodiment, the lead body 18 is coupled via the suture sleeve 48 to the access vessel into the heart 12, for example the left subclavian vein 28.

Figure 2A:
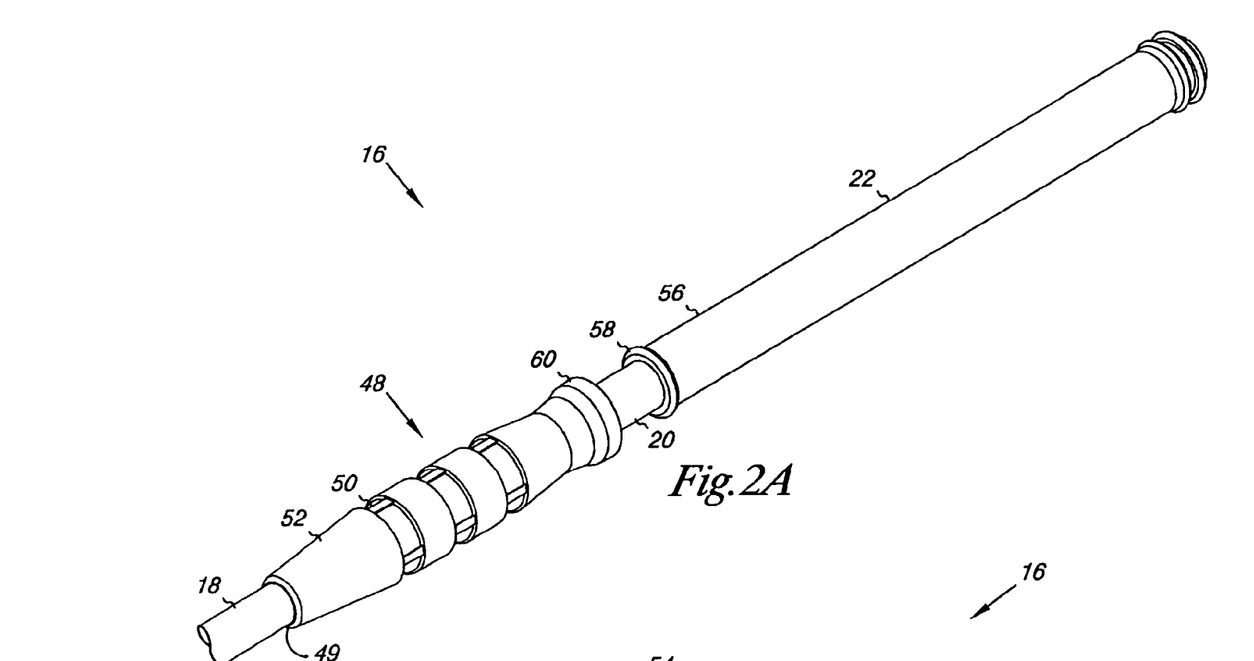
FIG. 2A is an exploded perspective view of a portion of a lead assembly according to a first embodiment of the present invention.
Figure 2B:
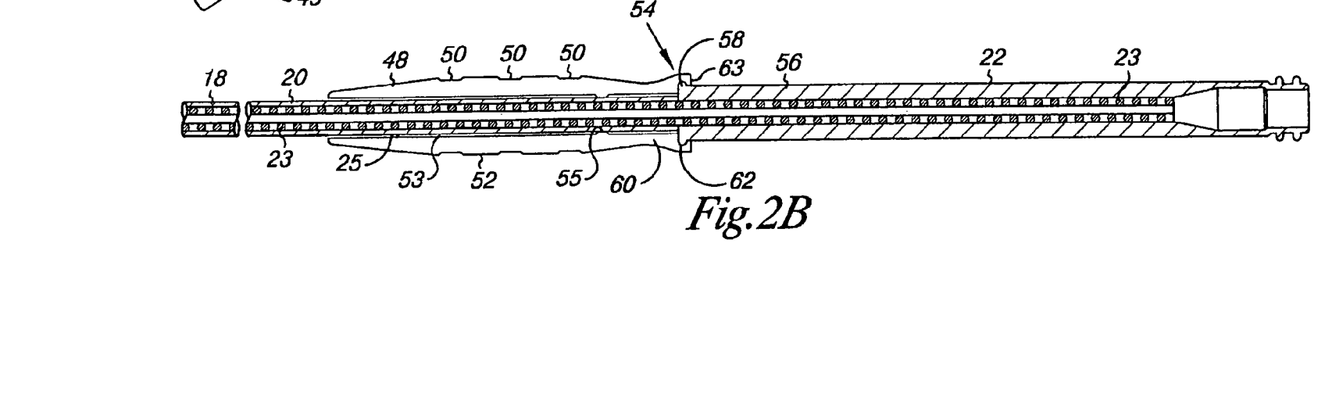
FIG. 2B is a cross-sectional view of the lead assembly of FIG. 2A.

FIG. 2A shows a perspective view of the lead assembly 16 according to one embodiment of the invention. FIG. 2B shows a cross-sectional view of the lead assembly 16 of FIG. 2A. As shown, the terminal connector 22 is located near the proximal end 20 of the flexible elongated lead body 18. The lead body 18 has an inner conductive coil 23 surrounded by an outer insulating layer 25. The suture sleeve 48 is a tubular member with a central bore 49 therethrough for receiving the lead body 18. The suture sleeve 48 is mounted to the lead body 18 distal to the terminal connector 22. In one embodiment, the suture sleeve 48 is provided with a series of grooves 50 in an outer surface 52. Sutures positioned in the grooves 50 and tied around the suture sleeve 48 secure the suture sleeve 48 to the surrounding tissue without exerting undue compression on the lead body 18. In one embodiment, an inner surface 53 of the suture sleeve 48 is provided with at least one protrusion 55. Protrusion 55 acts as a stand-off, reducing sliding friction between the lead body 18 and the inner surface 53 of the suture sleeve 48.

The suture sleeve 48 is detachably coupled to the terminal connector 22 via a separable anchor mechanism 54. In one embodiment, the anchor mechanism 54 is a mechanical interlock between the suture sleeve 48 and the terminal connector 22. A distal end 56 of the terminal connector 22 is provided with a first coupling feature, such as an annular ridge 58. A proximal end 60 of the suture sleeve 48 is provided with a mating feature, such as an annular indentation or recess 62, which is complementary to the ridge 58. The ridge 58 is receivable in the recess 62 to detachably couple the suture sleeve 48 to the terminal connector 22. As shown in FIG. 2B, the indentation 62 includes a lip 63, which contacts and releasably couples to the trailing surface of the ridge 58. The anchor mechanism 54, in an unseparated state, couples the suture sleeve 48 to the terminal connector 22 so that the suture sleeve 48 is prevented from sliding along the lead body 18. In this example, the suture sleeve 48 is stationary with respect to the terminal connector 22. The anchor mechanism 54 is separated by forcibly sliding the suture sleeve 48 distally or away from the terminal connector 22 with sufficient force to eject or "pop" the ridge 58 past the lip 63 and out of the recess 62. When the anchor mechanism 54 is in a separated state, the suture sleeve 48 is slidable along the length of the lead body 18.

According to other embodiments, the anchoring mechanism 54 may be a hemispherical protrusion and a complementary recess or other positive and complementary negative contours on the surface of the terminal connector 22 and the suture sleeve 48. According to still other embodiments, the anchor mechanism 54 may be a hook and eye, a bayonet, a snap-fit, an inflatable bladder or donut, or other suitable means for detachably coupling the suture sleeve 48 to the terminal connector 22.

Figure 3:
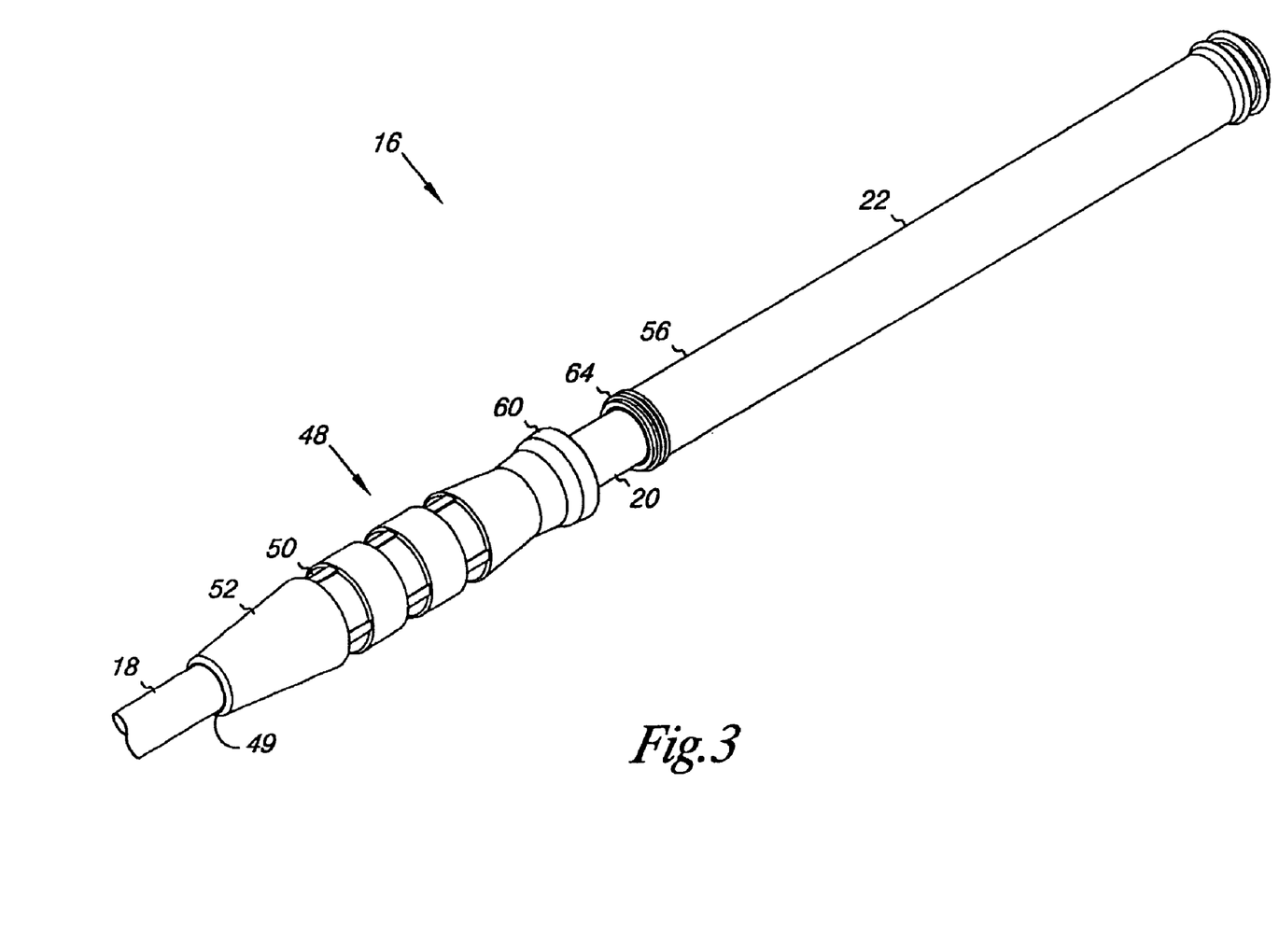
FIG. 3 is a cross-sectional view of a portion of a lead assembly according to a second embodiment of the present invention.

FIG. 3 shows a lead assembly 16 according to a second embodiment of the present invention in which the distal end 56 of the terminal connector 22 is provided with a threaded feature 64 and the proximal end 60 of the suture sleeve 48 is provided with a complementary threaded feature (not shown). The suture sleeve 48 may be rotated about the lead body 18 in a first direction to cause the suture sleeve threaded feature to engage the terminal connector threaded feature 64. Doing so secures the suture sleeve 48 to the terminal connector 22. The suture sleeve 48 may be rotated about the lead 18 in a second direction to disengage the threads 64 and reposition the suture sleeve 48 along the lead body 18.

The terminal connector 22 may be coupled to the suture sleeve 48 via the anchor mechanism 54 prior to the implantation procedure. Throughout the procedure, the suture sleeve 48 is reliably located adjacent the terminal connector 22. The anchor mechanism 54, in the active or un-separated state, prevents the suture sleeve 48 from sliding distally along the lead body 18. Specifically, the anchor mechanism 54 prevents the suture sleeve 48 from sliding distally along the lead body 18 and into the aperture 27 in the left subclavian vein 28. Such a "loss" normally requires the physician to retrieve the suture sleeve, a tedious, time-consuming, and potentially dangerous activity to undertake during the implantation procedure. However, a lead assembly 16 according to the present embodiment reliably locates the suture sleeve 48 adjacent the terminal connector 22 throughout the implantation procedure and reduces the likelihood of the suture sleeve 48 sliding distally along the lead body 18 and into the aperture 27. Following implantation, the suture sleeve 48 is easily disengaged from the terminal connector 22 to separate the anchor mechanism 54 and relocated distally along the lead body 18 to an appropriate fixation location for suturing to the surrounding tissue.

Figure 4A:
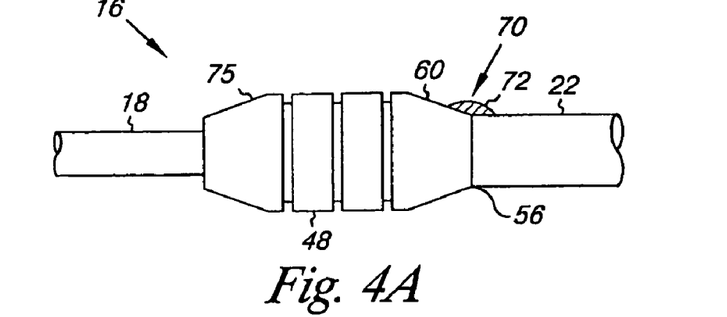
FIGS. 4A–4D are perspective views of a portion of a lead assembly according to a third embodiment of the present invention.
Figure 4B:
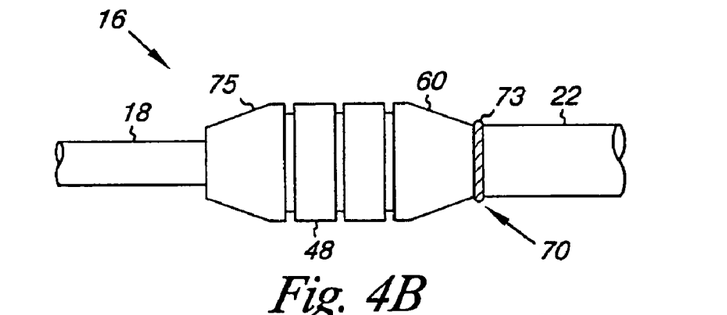

FIG. 4A shows a portion of a lead assembly 16 according to a third embodiment of the present invention in which the suture sleeve 48 is detachably coupled to the terminal connector 22 via an adhesive bond or adhesive anchoring mechanism 70. The adhesive anchoring mechanism 70 secures the proximal end 60 of the suture sleeve 48 to the distal end 56 of the terminal connector 22. As shown in FIG. 4A, the anchor mechanism 70 is formed from a bead 72 of adhesive material. According to another embodiment, as shown in FIG. 4B, the anchor mechanism 70 is provided via a ring 73 of adhesive material. According to one embodiment, the anchor mechanism 70 is provided via a biocompatible adhesive. According to another embodiment, the anchor mechanism 70 is provided via a biocompatible silicone glue. According to another embodiment, either or both of the suture sleeve 48 and the terminal connector 22 are provided with an adhesive region for adhering to the other of the suture sleeve 48 or the terminal connector 22. Throughout the implantation, the suture sleeve 48 is coupled to the terminal connector 22 via the adhesive anchoring mechanism 70. Following implantation, the adhesive anchor mechanism 70 is separated to uncouple the suture sleeve 48 from the terminal connector 22.

Figure 4C:
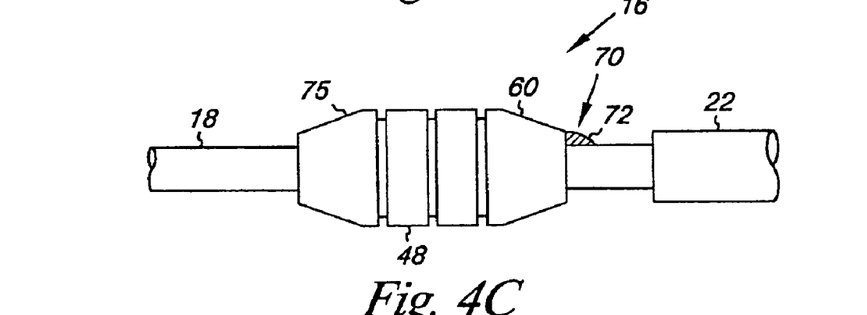
Figure 4D:
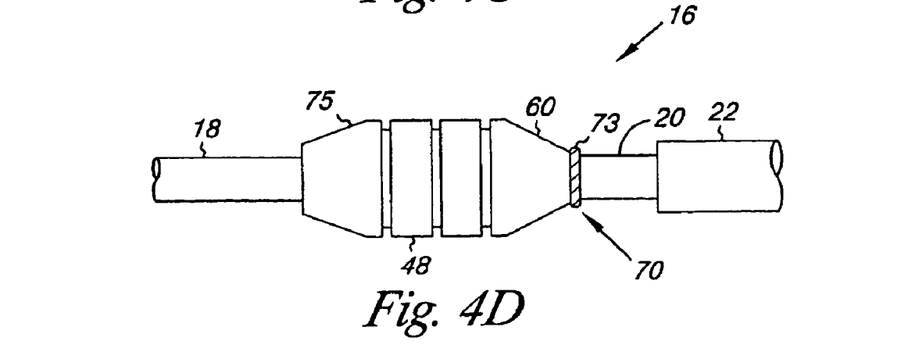

FIGS. 4C and 4D show another embodiment, in which the adhesive anchoring mechanism 70 adheres the suture sleeve 48 to the lead body 18. The bead 72 of adhesive material is positioned to adhere the suture sleeve 48 to the lead body 18, as shown in FIG. 4C, or the ring of adhesive material 73 is positioned to adhere the suture sleeve 48 to the lead body 18, as shown in FIG. 4D. According to another embodiment, the adhesive anchoring mechanism 70 could be positioned at the proximal end 60 of the suture sleeve 48 to adhere the suture sleeve 48 to the lead body 18.

Figure 5A:
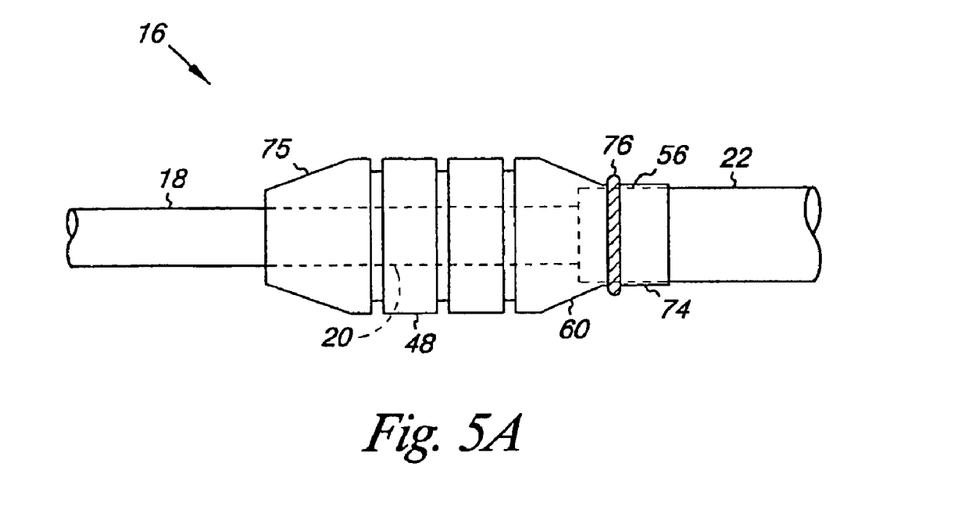
FIGS. 5A–5B are perspective views of a portion of a lead assembly according to a fourth embodiment of the present invention.

FIG. 5A shows a portion of the lead assembly 16 according to a fourth embodiment of the present invention. As shown in FIG. 5A, the proximal end 60 of the suture sleeve 48 has an inner diameter greater than an outer diameter of the distal end 56 of the terminal connector 22. The proximal end 60 of the suture sleeve 48 is positioned to overlap the distal end 56 of the terminal connector 22 at a region of overlap 74. The lead assembly 16 further includes a resilient ring member 76 mounted to the lead body 18 at the region of overlap 74. The ring member 76 is sized and configured to compress the proximal end 60 of the suture sleeve 48 onto the distal end 56 of the terminal connector 22 with sufficient force to retain the suture sleeve 48 in a stationary position. In this manner, the suture sleeve 48 is coupled to the terminal connector 22 and prevented from sliding distally along the lead body 18.

Following implantation of the lead assembly 16, the ring member 76 is slid or rolled away from the area overlap 74. The suture sleeve 48 is slid distally along the lead body 18 away from the terminal connector 22 to an appropriate position. Optionally, the suture sleeve 48 is pulled away from the terminal connector 22 to overcome the compressive force of the ring member 76 and uncouple the suture sleeve 48 from the terminal connector 22. The ring member 76 may be detached from the lead assembly 16 or remain permanently implanted.

Figure 5B:
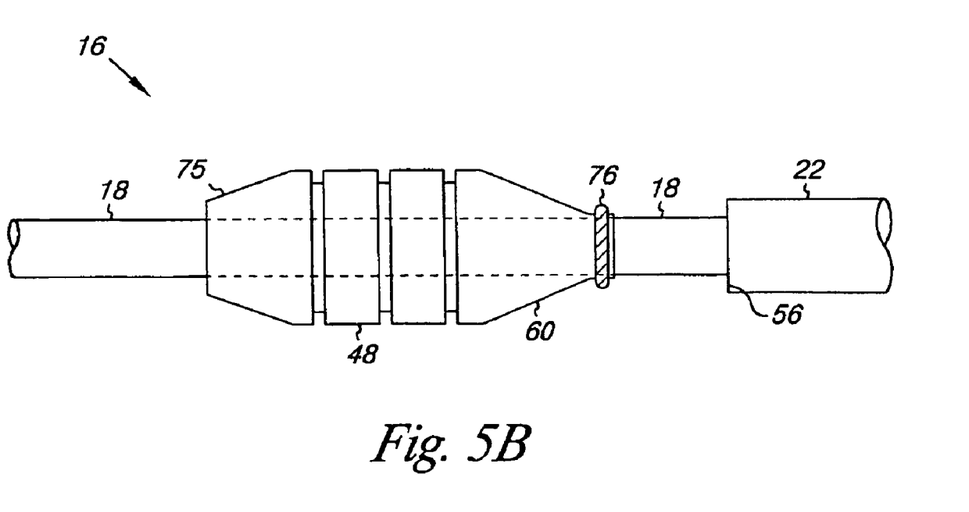

FIG. 5B shows another embodiment of the present invention, in which the ring member 76 is positioned over the proximal end 60 of the suture sleeve 48 to compress the suture sleeve 48 directly onto the lead body 18.

Figure 6A:
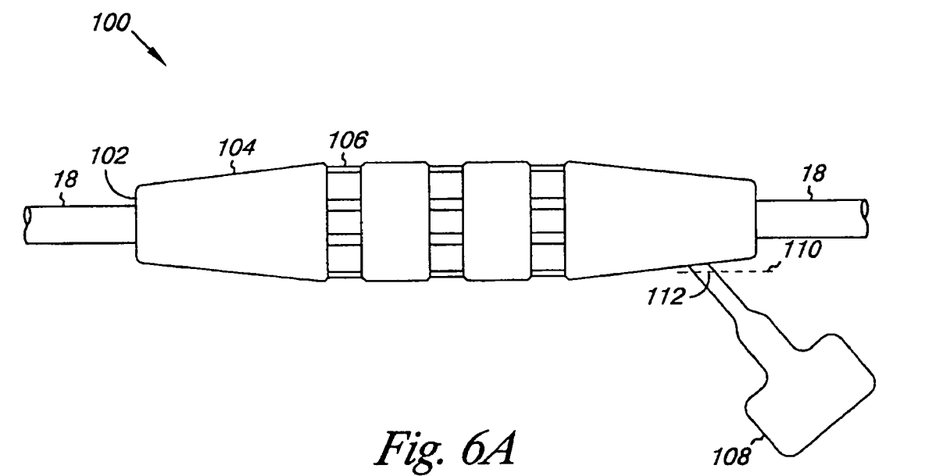
FIG. 6A is a perspective view of a portion of a lead assembly according to a fifth embodiment of the present invention.

FIG. 6A shows a pacing lead stabilizer 100 for use with the pacing lead assembly 16 according to a fifth embodiment of the present invention. According to one embodiment, the pacing lead stabilizer 100 is a suture sleeve having a central bore 102 therethrough for slidably receiving the pacing lead body 18 (not shown). An exterior surface 104 of the suture sleeve 100 is provided with suture grooves 106 for receiving sutures. The suture sleeve 100 includes an anchoring tab or wing 108 separable or detachable from the sleeve 100 at line 110. Line 110 extends along a weak region 112 of the tab 108. According to one embodiment, the weak region 112 is provided with perforations to facilitate detachment of the tab 108 from the suture sleeve 100 along line 110. In other embodiments, the weak region 112 is pre-stressed, for example by bending or folding, so as to facilitate detachment of the tab 108 from the suture sleeve 100. According to other embodiments, the weak region 112 is on the suture sleeve 100 so that substantially the entire tab 108 is removable from the suture sleeve 100. According to one embodiment, the tab 108 is from about 1 to 2 cm long and from about 1 to 2 cm wide.

The anchoring tab 108 is sized to prevent the suture sleeve 100 from sliding distally along the lead body 18 into the aperture 27 in the left subclavian vein 28 and becoming lost. While the anchoring tab 108 is yet attached to the suture sleeve 100, the suture sleeve 100 has a reduced sliding length along the lead body 18, i.e., the suture sleeve 100 may only slide between the terminal connector 22 and the aperture 27 in the left subclavian vein 28. After the suture sleeve 100 has been sutured to surrounding tissue, the anchoring tab 108 may be detached from the sleeve 100 along line 110 and discarded. The remaining suture sleeve 100 has a reduced profile, providing increased patient comfort and improved appearance. Optionally, the tab 108 may not be detached or separated from the sleeve body 100 but rather remain permanently implanted.

Figure 6B:
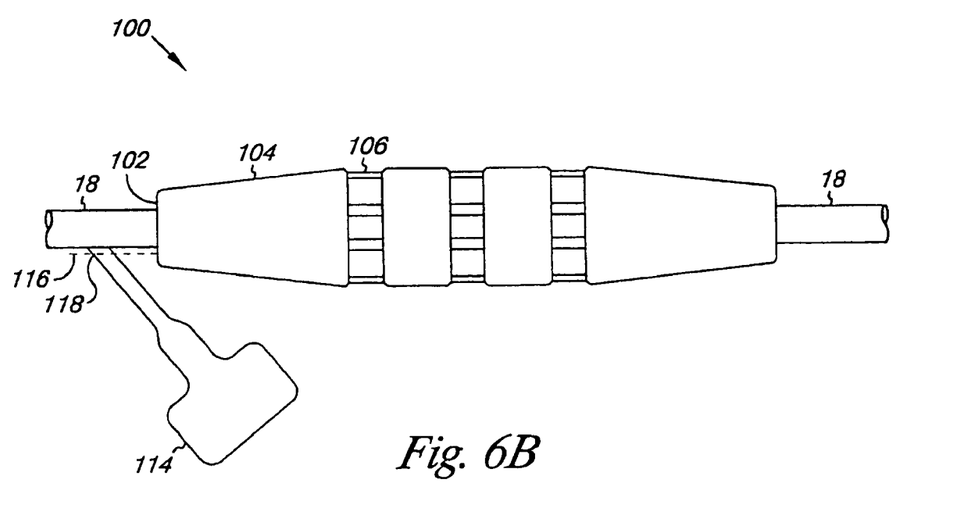
FIG. 6B is a perspective view of a portion of a lead assembly according to a sixth embodiment of the present invention.

FIG. 6B shows a sixth embodiment of a pacing lead stabilizer 100 in accordance with the present invention, in which an anchoring tab 114 is located on the lead body 18 distal to the suture sleeve 100 and is detachable from the lead body 16 along a line 116. The line 116 may extend along a weakened region 118 of the anchoring tab 114, as described with respect to FIG. 6A.

Figure 7A:
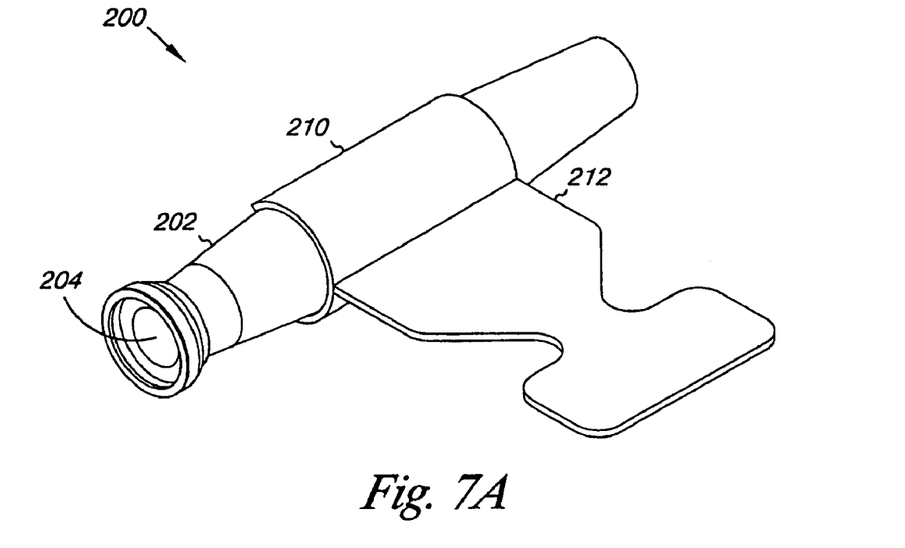
FIG. 7A is a perspective view of a pacing lead stabilizer assembly according to a seventh embodiment of the present invention.
Figure 7B:
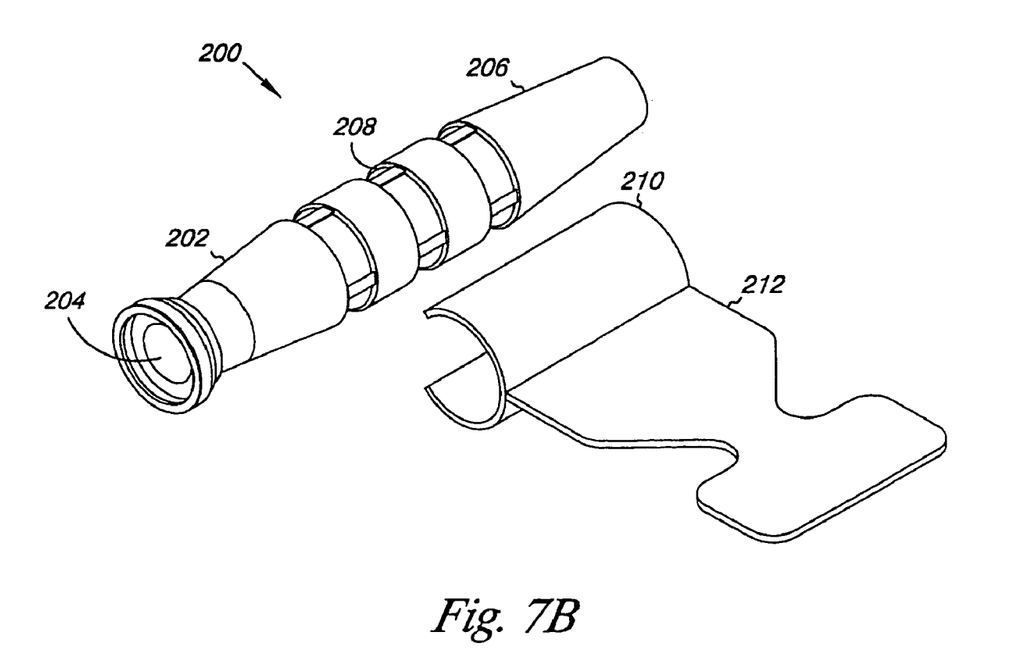
FIG. 7B is an exploded perspective view of the pacing lead stabilizer assembly of FIG. 7A.

FIGS. 7A and 7B show a pacing lead stabilizer assembly 200 for use with an implantable medical device according to a seventh embodiment of the present invention. The pacing lead stabilizer assembly 200 includes a suture sleeve 202 having a central bore 204 therethrough for receiving a lead body (not shown). An outer surface 206 of the suture sleeve 202 is provided with suture grooves 208 for receiving sutures. The pacing lead stabilizer assembly 200 further includes an anchoring member or C-ring 210 detachably coupleable to the suture sleeve 202. The C-ring 210 is elongated and has a C-shaped cross section. An anchoring wing or tab 212 is supported on the C-ring 210.

Prior to implantation, the C-ring 210 is mounted to the suture sleeve 202. The mounted C-ring 210 obscures the suture grooves 208 of the suture sleeve 202. Throughout the implantation procedure, the tab 212 on the C-ring 210 prevents the pacing lead stabilizer assembly 200 from sliding through the aperture 27 in the left subclavian 28 and becoming lost. Following implantation, the C-ring 210 is detached from the suture sleeve 202 to reveal the suture grooves 208.

Removal of the C-ring 210 reduces the size and profile of the pacing lead stabilizer assembly 200, increasing patient comfort and improving appearance. As the C-ring 210 must be removed from the suture sleeve 202 prior to suturing, there is a reduced likelihood of accidental permanent implantation of the anchoring member 210.

A pacing lead stabilizer according to one embodiment of the present invention includes a first anchor as described with respect to FIGS. 1–5B and a second anchor as described with respect to FIGS. 6A–7B. The first anchor retains the pacing lead stabilizer in a secure position throughout an implantation procedure, preferably adjacent the terminal connector. Once the first anchor is detached or separated so that the pacing lead stabilizer is slidable along the lead, the second anchor prevents the pacing lead stabilizer from sliding into an aperture in the adjacent access vessel and becoming lost.

Figure 8A:
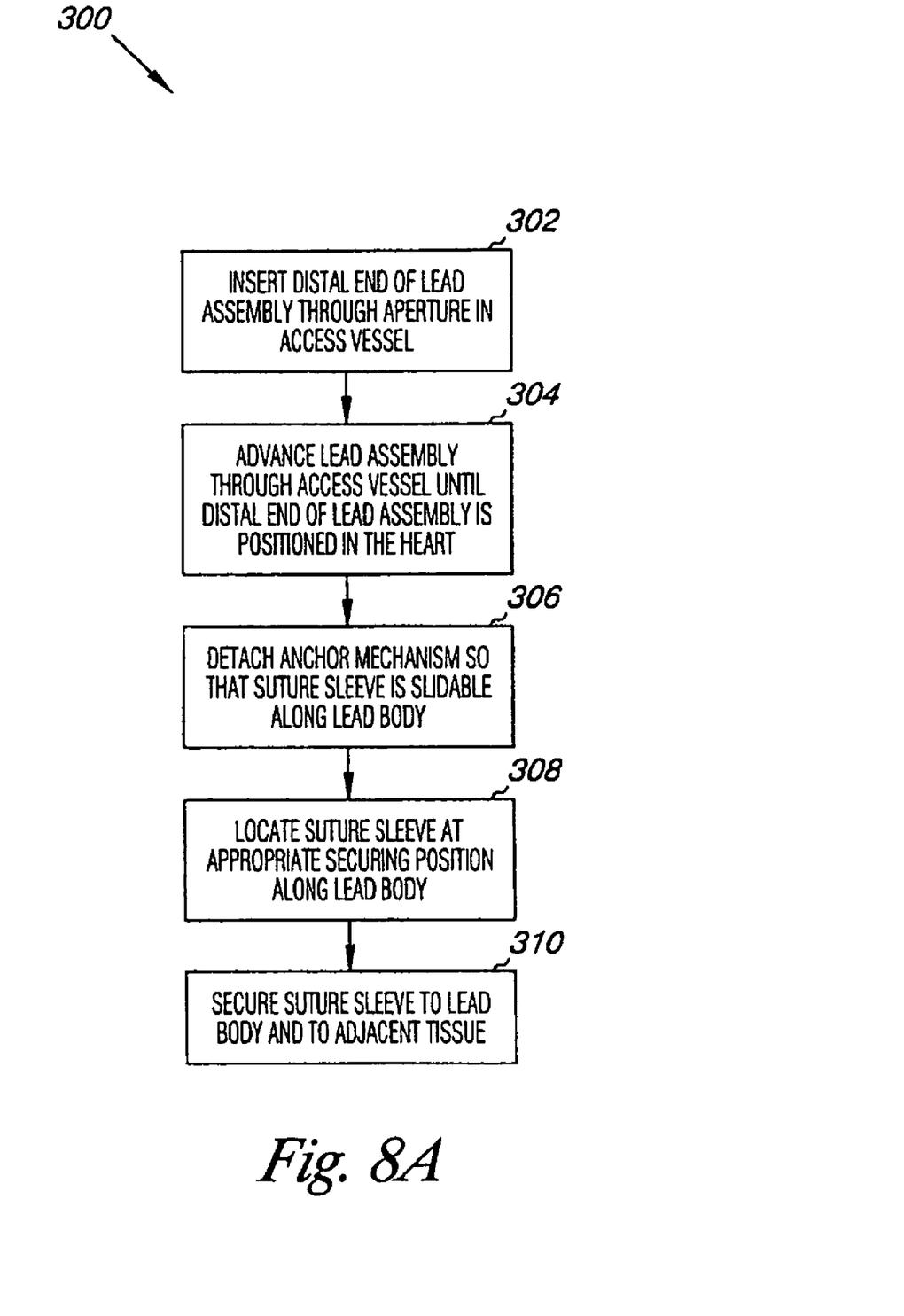
FIG. 8A is a flowchart depicting a method of implanting a lead assembly according to one embodiment of the present invention.

FIG. 8A is a flowchart depicting a method 300 of implanting a lead assembly according to one embodiment of the present invention. As shown in FIG. 8A, the distal end of the lead assembly is inserted through an aperture in an access vessel (block 302). The lead assembly is advanced through the access vessel until the distal end of the lead assembly is positioned in the heart (block 304). The anchor mechanism is detached so that the suture sleeve is slidable along the lead body (block 306). The suture sleeve is located at an appropriate position along the lead body for securing the lead body to the surrounding tissue (block 308). The suture sleeve is secured to the surrounding tissue and to the lead body (block 310).

Figure 8B:
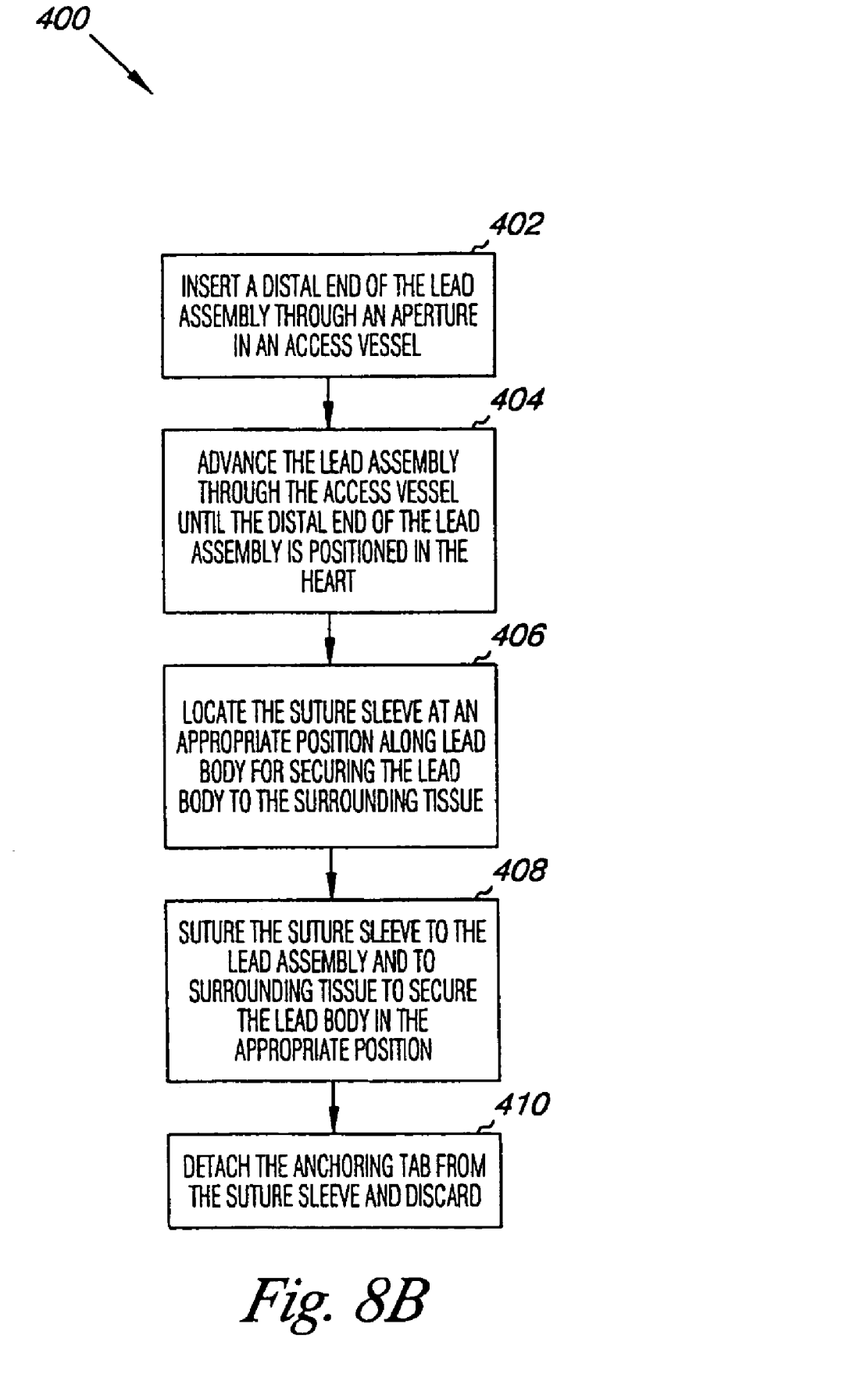
FIG. 8B is a flowchart depicting a method of implanting a lead assembly according to another embodiment of the present invention.

FIG. 8B is a flowchart depicting a method 400 of implanting a lead assembly according to another embodiment of the present invention. As shown in FIG. 8B, the distal end of the lead assembly is inserted through an aperture in an access vessel (block 402). The lead assembly is advanced through the access vessel until the distal end of the lead assembly is positioned in the heart (block 404). The suture sleeve is located at an appropriate position along the lead body for securing the lead body to the surrounding tissue (block 406). The suture sleeve is sutured to the lead assembly and to surrounding tissue to secure the lead body in the appropriate position (block 408). The anchoring tab is detached from the suture sleeve and discarded (block 410).

While the present invention is described with respect to an endocardial lead, the various embodiments are also applicable to use with various epicardial leads. Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A lead assembly for use with an implantable cardiac function management system, the lead assembly comprising:
    an elongated flexible pacing lead having a proximal end and a distal end;
    a terminal connector connected to the proximal end of the pacing lead and having a distal end formed with a first coupling feature; and
    a pacing lead stabilizer having a central bore mounted on the pacing lead and slidable along the pacing lead, the pacing lead stabilizer having a stabilizer proximal end formed with a mating feature complementary to the first coupling feature, such that the pacing lead stabilizer is releasably coupleable to the terminal connector.

2. The lead assembly of claim 1 wherein the pacing lead stabilizer includes a plurality of grooves formed on an outer surface for receiving suture threads.

3. The lead assembly of claim 1 wherein the first coupling feature is an annular ridge and the mating feature is an annular recess formed in the bore at the stabilizer proximal end, wherein the annular ridge is receivable in the annular recess.

4. The lead assembly of claim 3 wherein the recess includes a lip adapted to contact a trailing surface of the annular ridge.

5. The lead assembly of claim 1 wherein the first coupling feature and the second surface are complementary threads, such that the pacing lead stabilizer is threadably coupleable to the terminal connector.

6. The lead assembly of claim 1 wherein the central bore includes at least one radial protrusion, the protrusion adapted to contact an outer surface of the pacing lead.

7. A lead assembly for use with an implantable cardiac function management system, the lead assembly comprising:
    an elongated flexible pacing lead having an electrode at a distal end and a terminal connector at a proximal end;
    a pacing lead stabilizer having a central bore, the stabilizer coupled to the lead such that the lead extends through the central bore; and
    separable anchor mechanism means for restricting linear movement of the pacing lead stabilizer with respect to the pacing lead wherein the anchor mechanism means comprises a separable mechanical interlock coupling the pacing lead stabilizer to the terminal connector.

8. The lead assembly of claim 7 wherein the mechanical interlock comprises a recess formed on a proximal end of the pacing lead stabilizer and a matching recess formed on a distal end of the terminal connector.

9. The lead assembly of claim 7 wherein the anchor mechanism means further comprises a threaded feature formed on a distal end of the terminal connector and a complementary threaded feature formed on a proximal end of the pacing lead stabilizer.

10. The lead assembly of claim 7 wherein the mechanical interlock further includes a member selected from the group consisting of: a hook and eye, a bayonet, a snap-fit, and an inflatable bladder.

11. The lead assembly of claim 7 wherein the anchor mechanism means further comprises a separable adhesive bond coupling the pacing lead stabilizer to the pacing lead.

12. The lead assembly of claim 7 wherein the anchor mechanism means further comprises a separable adhesive bond coupling the proximal end of the pacing lead stabilizer to the terminal connector.

13. The lead assembly of claim 7 wherein the anchor mechanism means further comprises an elastic ring encircling the pacing lead stabilizer, the elastic ring exerting sufficient force on the pacing lead stabilizer to compress the pacing lead stabilizer about the pacing lead and generate a frictional force sufficient to retain the pacing lead stabilizer with respect to the pacing lead.

14. The lead assembly of claim 13 wherein the pacing lead stabilizer further comprises a proximal end overlapping a distal end of the terminal connector, wherein the elastic ring is positioned around the region of overlap to compress the pacing lead stabilizer onto the terminal connector.

15. The lead assembly of claim 7 wherein the anchor mechanism means further comprises a detachable tab extending from the pacing lead stabilizer, the tab sized to prevent the pacing lead stabilizer from entering an opening in an access vessel.

16. The lead assembly of claim 15 wherein the tab laterally extends from the pacing lead stabilizer a distance of from about 1 cm to about 2 cm.

17. The lead assembly of claim 15 wherein the tab has a length of from about 1 cm to about 2 cm and a width of from about 1 cm to about 2 cm.

18. The lead assembly of claim 15 wherein the anchor mechanism means further comprises a detachable C-ring supporting the tab and positioned on the pacing lead stabilizer to obscure a plurality of suture grooves.

19. A method of implanting a pacing lead assembly, the pacing lead assembly including a pacing lead having a surface electrode at a distal end, a terminal connector at a proximal end, a pacing lead stabilizer having a central bore slidably mounted to the pacing lead, and an anchor mechanism for restricting linear motion of the pacing lead stabilizer with respect to the pacing lead, the method comprising:

inserting the distal end of the pacing lead through an aperture in an access vessel to the heart;

advancing the pacing lead through the access vessel until the distal end of the pacing lead is positioned in or near the heart;

separating the anchor mechanism to allow full linear motion of the pacing lead stabilizer with respect to the pacing lead;

locating the pacing lead stabilizer at an appropriate position along the pacing lead for securing the pacing lead to the surrounding tissue; and suturing the pacing lead stabilizer to the surrounding tissue and to the pacing lead to resist dislocation of the pacing lead retaining the pacing lead stabilizer adjacent the terminal connector throughout insertion and advancement of the pacing lead through the access vessel.

20. The method of claim 19 further comprising sliding the pacing lead stabilizer distally from the terminal connector to detach the pacing lead stabilizer from the terminal connector.

21. The method of claim 19 further comprising rotating the pacing lead stabilizer with respect to the terminal connector to detach the pacing lead stabilizer from the terminal connector.

22. The method of claim 19 further comprising removing a tab extending laterally from the pacing lead stabilizer.

23. The method of claim 19 further comprising removing a tab extending from the pacing lead.

24. The method of claim 19 further comprising breaking an adhesive bond between the pacing lead stabilizer and the terminal connector.

25. The method of claim 19 further comprising breaking an adhesive bond between the pacing lead stabilizer and the pacing lead.

26. The method of claim 19 further comprising separating the anchor mechanism to allow full linear motion of the pacing lead stabilizer with respect to the pacing lead then locating the pacing lead stabilizer at an appropriate position along the pacing lead for securing the pacing lead to the surrounding tissue.

27. The method of claim 19 further comprising locating the pacing lead stabilizer at an appropriate position along the pacing lead for securing the pacing lead to the surrounding tissue then separating the anchor mechanism to allow full linear motion of the pacing lead stabilizer with respect to the pacing lead.

* * * * *